(12) United States Patent
Ryan et al.

(10) Patent No.: US 10,888,408 B2
(45) Date of Patent: Jan. 12, 2021

(54) PACKAGING FOR DRY TISSUE PROSTHETIC HEART VALVE

(71) Applicant: Medtronic Vascular, Inc., Santa Rosa, CA (US)

(72) Inventors: Raymond Ryan, Limerick (IE); David Clarke, Galway (IE); Kshitija Garde, Fullerton, CA (US); Ya Guo, Irvine, CA (US); Benjamin Wong, Irvine, CA (US); Yogesh Darekar, Irvine, CA (US); Luke Lehmann, Newport Beach, CA (US); Wei Wang, Garden Grove, CA (US); Laura McKinley, Tustin, CA (US); Paul Devereux, Galway (IE); Joshua Dudney, Mission Viejo, CA (US); Tracey Tien, Irvine, CA (US); Karl Olney, Tustin, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 216 days.

(21) Appl. No.: 15/968,847

(22) Filed: May 2, 2018

(65) Prior Publication Data

US 2018/0318060 A1    Nov. 8, 2018

Related U.S. Application Data

(60) Provisional application No. 62/500,046, filed on May 2, 2017.

(51) Int. Cl.
*A61F 2/00* (2006.01)
*B65D 81/22* (2006.01)
(Continued)

(52) U.S. Cl.
CPC .......... *A61F 2/0095* (2013.01); *A61F 2/2412* (2013.01); *A61L 2/206* (2013.01);
(Continued)

(58) Field of Classification Search
CPC ........ B65D 51/20; B65D 81/24; B65D 81/22; B65B 55/54; A61F 2/0095; A61F 2/2418
See application file for complete search history.

(56) References Cited

U.S. PATENT DOCUMENTS 4,211,325 A * 7/1980 Wright .................. A61F 2/0095
206/438
5,720,391 A * 2/1998 Dohm .................... A61F 2/0095
206/363
(Continued)

FOREIGN PATENT DOCUMENTS

WO    WO 1998036992 A1    8/1998

OTHER PUBLICATIONS

Xuejun Zhu, Yi Zhang, Jun Deng, Xujun Luo, Effect of Glycerol on the Properties of the Corss-Linked Polyvinyl Alcohol Hydrogel Beads, Jan. 9, 2018, Chemistry Europe, vol. 3 Issue 2, pp. 467-470.*
(Continued)

*Primary Examiner* — J. Gregory Pickett
*Assistant Examiner* — Tia Cox
(74) *Attorney, Agent, or Firm* — Dicke, Billig & Czaja, PLLC

(57) ABSTRACT

A "dry" packaging in which a prosthetic heart valve is packaged within a container with hydrogel that can be provided in many forms. Certain embodiments include hydrogel that is preloaded with glycerol or the like. The hydrogel regulates the humidity within the container through a diffusion-driven mechanism if a gradient of humidity between the inside and the outside of the hydrogel exists. Humidity regulation is important to prevent the tissue of the valve structure from drying out. When the partially-hydrated hydrogel is present within container, which is saturated with air of a predefined humidity, the water molecules from the air will be absorbed by the hydrogel if the air humidity is high (i.e. when the thermodynamics favor hydrogel hydra-
(Continued)

tion) or vice versa. Various embodiments are configured to also house at least a portion of a delivery device for delivering the prosthetic heart valve.

20 Claims, 13 Drawing Sheets

(51) Int. Cl.
*B65D 81/18* (2006.01)
*A61F 2/24* (2006.01)
*A61L 2/26* (2006.01)
*A61L 2/20* (2006.01)
*A61L 2/08* (2006.01)

(52) U.S. Cl.
CPC ................ *A61L 2/26* (2013.01); *B65D 81/18* (2013.01); *B65D 81/22* (2013.01); *A61F 2/2418* (2013.01); *A61L 2/08* (2013.01); *A61L 2/208* (2013.01); *A61L 2202/182* (2013.01); *A61L 2202/21* (2013.01)

(56) References Cited

U.S. PATENT DOCUMENTS

| | | | |
|---|---|---|---|
| 6,921,179 B2* | 7/2005 | Diak Ghanem | A47G 19/2227 206/217 |
| 7,712,606 B2 | 5/2010 | Salahieh et al. | |
| 7,748,525 B2* | 7/2010 | Boyd | B65B 3/18 206/213.1 |
| 9,295,549 B2* | 3/2016 | Braido | A61F 2/2418 |
| 2002/0120328 A1* | 8/2002 | Pathak | A61F 2/24 623/2.2 |
| 2003/0029739 A1* | 2/2003 | Riemenschneider | B65D 81/266 206/204 |
| 2007/0050014 A1 | 3/2007 | Johnson | |
| 2007/0056149 A1 | 3/2007 | Axel | |
| 2007/0061008 A1 | 3/2007 | Salahieh et al. | |
| 2007/0065968 A1* | 3/2007 | Kok | H04R 31/00 438/53 |
| 2008/0102439 A1 | 5/2008 | Tian et al. | |
| 2010/0252470 A1 | 10/2010 | Ryan et al. | |
| 2011/0198244 A1* | 8/2011 | Murad | A61F 2/0095 206/210 |
| 2012/0158128 A1 | 6/2012 | Gautam et al. | |
| 2014/0158557 A1* | 6/2014 | Dolan | B65D 79/005 206/0.7 |
| 2014/0202908 A1 | 7/2014 | Liburd | |
| 2015/0314942 A1* | 11/2015 | Gwen | B01D 53/0407 206/204 |
| 2016/0207897 A1* | 7/2016 | Wood | C07D 307/50 |
| 2016/0270897 A1* | 9/2016 | Whiting | C12M 25/02 |
| 2018/0318061 A1 | 11/2018 | Clark et al. | |

OTHER PUBLICATIONS

International Search Report and Written Opinion for related International Application No. PCT/US2018/030587 dated Aug. 13, 2018 (13 pgs.).

PCT Transmittal of the International Search Report and the Written Opinion from Application No. PCT/US2018/030575 dated Aug. 31, 2018.

* cited by examiner

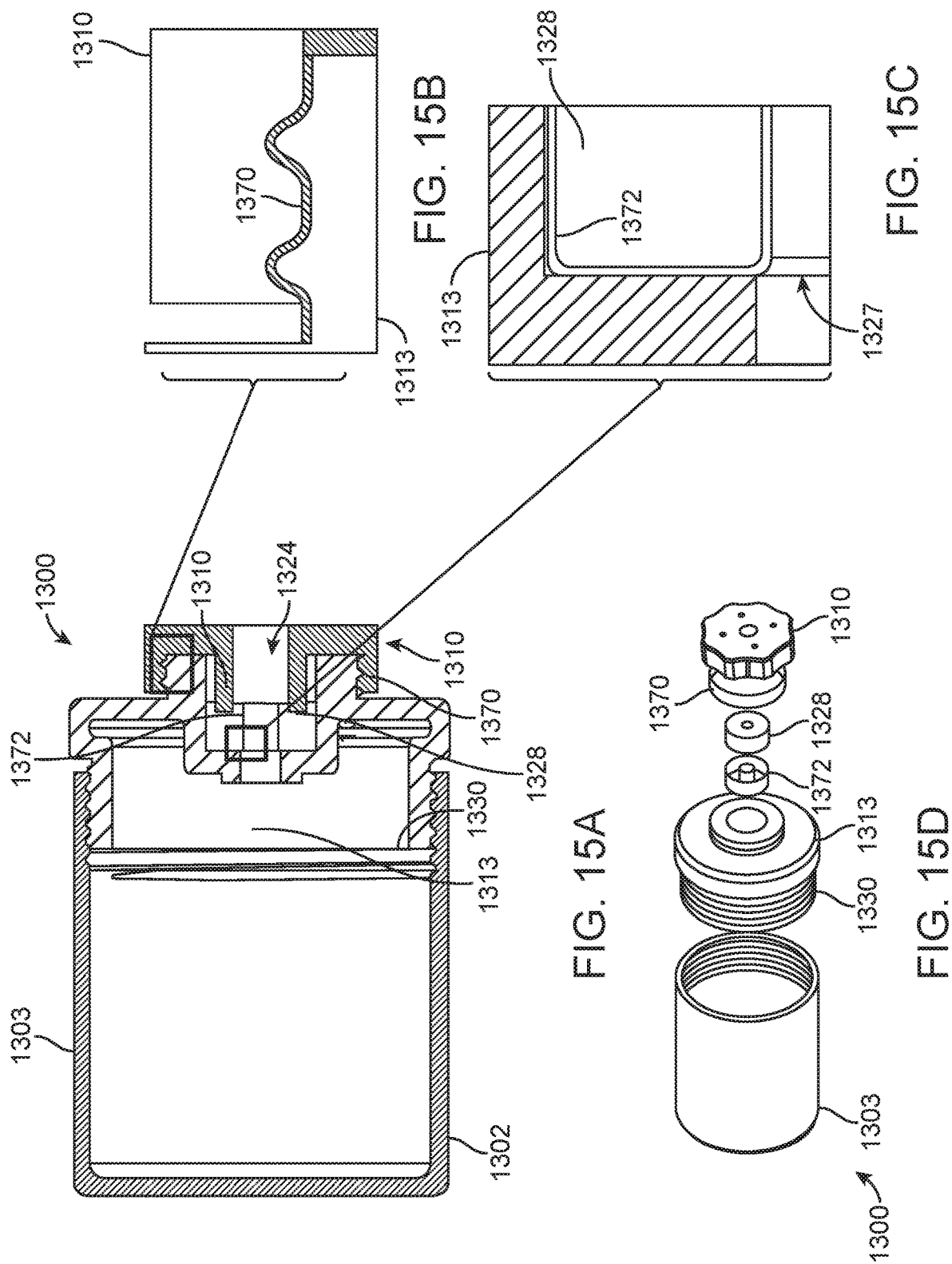

PACKAGING FOR DRY TISSUE PROSTHETIC HEART VALVE

CROSS-REFERENCE TO RELATED APPLICATIONS

This Non-Provisional Patent Application claims the benefit of the filing date of U.S. Provisional Patent Application Ser. No. 62/500,046, filed May 2, 2017, the entire teachings of which are incorporated herein by reference.

BACKGROUND

Disclosed embodiments relate to packaging for a "dry" tissue prosthetic heart valve either with or without a portion of a delivery device. Methods of packaging transcatheter heart valves with or without the portion of the delivery device are also disclosed.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter of a delivery device, inserted inside a body lumen of the patient, such as the femoral artery, and delivered to a desired location in the heart where the valve prosthesis is then deployed.

Known valve prostheses include a stent frame supporting a valve structure. The valve structure can assume a variety of forms, and can be formed, for example, from tissue made from one or more biocompatible synthetic materials, synthetic polymers, autograft tissue, homograft tissue, xenograft tissue, or one or more other suitable materials. In some embodiments, the valve structure can be formed, for example, from bovine, porcine, equine, ovine and/or other suitable animal tissues. The valve structure can be formed from heart valve tissue, pericardium, and/or other suitable tissue. In some embodiments, the valve structure can include or form one or more leaflets. For example, the valve structure can be in the form of a tri-leaflet bovine pericardium valve, a bi-leaflet valve, or another suitable valve.

Valve prostheses are often packaged in containers filled with solution, such as glutaraldehyde, for sterilizing and preserving the valve prosthesis prior to attachment to a delivery device for delivery to a patient. Sometimes, the valve prosthesis is preloaded on a distal portion of the delivery device, which are both packaged in the container. Some known packaging configurations include both wet and dry compartments; wherein the valve prosthesis is stored in a wet compartment loaded onto the delivery device component and the remainder of the delivery device component is secured in a dry compartment. In other valve prosthesis packaging, the valve prosthesis is packaged in a dry compartment, however, it has been found that transportation, storage and ethylene oxide (EtO) sterilization can dry out valve prosthesis tissue in these conditions.

The disclosed embodiments address problems and limitations with the related art.

SUMMARY

It has been found that transportation, storage and ethylene oxide (EtO) sterilization can dry out tissue of a prosthetic heart valve stored in "dry" packaging, which does not submerge the prosthetic heart valve in a preserving and/or sterilizing solution. Disclosed embodiments provide dry packaging for a prosthetic heart valve or other implant with or without a portion of a delivery device. Various disclosed packaging embodiments include a container including a first compartment housing the prosthetic heart valve and a second compartment housing hydrogel; wherein a semi-permeable membrane separates the first and second compartments. Optionally, the hydrogel, valve tissue and/or container are preloaded with glycerol or similar hydrator that maintains the hydration of the valve tissue. The hydrogel regulates the humidity within the container through the equilibration between humidity within the container and the hydrogel's ability to hold water. Humidity regulation is important to prevent the tissue of the valve structure from drying out. When the partially-hydrated hydrogel is present within container, which is saturated with air of a predefined humidity, the water molecules from the air will be either released or absorbed by the hydrogel through a diffusion-driven mechanism, if a gradient of humidity between the inside and the outside of the hydrogel exists. Various embodiments are configured to also house at least a portion of a delivery device for delivering the prosthetic heart valve.

BRIEF DESCRIPTION OF THE DRAWINGS

FIGS. 15A-15D are a collection of cross-sectional, enlarged and exploded views illustrating an alternate packaging.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted prosthetic heart valve, the terms "distal" and "outflow" are understood to mean downstream to the direction of blood flow, and the terms "proximal" or "inflow" are understood to mean upstream to the direction of blood flow.

As referred to herein, stented transcatheter prosthetic heart valves useful with and/or as part of the various systems, devices and methods of the present disclosure may assume a wide variety of different configurations, such as a bioprosthetic heart valve having tissue leaflets or a synthetic heart valve having polymeric, metallic or tissue-engineered leaflets, and can be specifically configured for replacing any of the four valves of the human heart. Thus, the stented prosthetic heart valve useful with the systems, devices, and methods of the present disclosure can be generally used for replacement of a native aortic, mitral, pulmonic or tricuspid valve, or to replace a failed bioprosthesis, such as in the area of an aortic valve or mitral valve, for example.

In general terms, the stented prosthetic heart valves of the present disclosure include a stent or stent frame having an internal lumen maintaining a valve structure (tissue or synthetic), with the stent frame having a normal, expanded condition or arrangement and collapsible to a compressed condition or arrangement for loading within a delivery device. The stent frame is normally constructed to self-deploy or self-expand when released from the delivery device. For example, the stents or stent frames are support structures that comprise a number of struts or wire segments arranged relative to each other to provide a desired compressibility and strength to the prosthetic heart valve. The struts or wire segments are arranged such that they are capable of self-transitioning from a compressed or collapsed condition to a normal, radially expanded condition. The struts or wire segments can be formed from a shape memory material, such as a nickel titanium alloy (e.g., nitinol). The stent frame can be laser-cut from a single piece of material, or can be assembled from a number of discrete components.

Figure 1A:
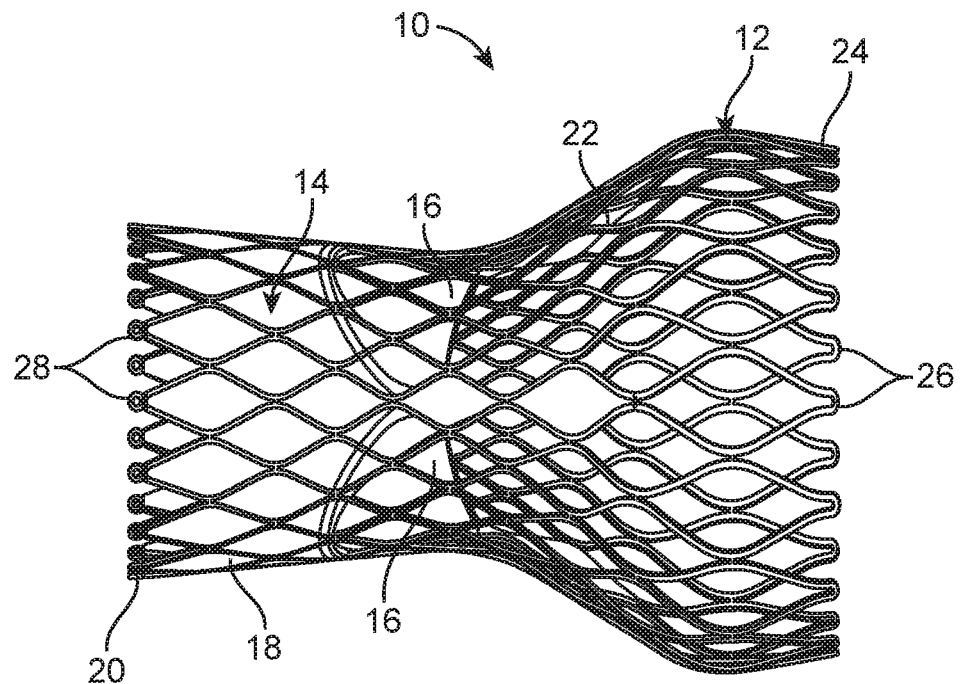
FIG. 1A is a side view of a stented prosthetic heart valve useful with systems, devices and methods of the present disclosure and in a normal, expanded condition.
Figure 1B:
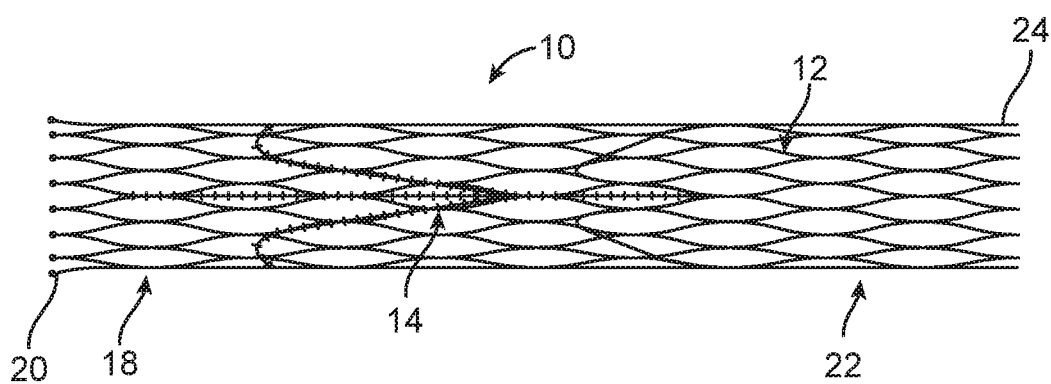
FIG. 1B is a side view of the prosthetic heart valve of FIG. 1A in a compressed condition.

With the above understanding in mind, one simplified, non-limiting example of a stented prosthetic heart valve 10 useful with systems, devices and methods of the present disclosure is illustrated in FIG. 1A. As a point of reference, the prosthetic heart valve 10 is shown in a normal or expanded condition in the view of FIG. 1A; FIG. 1B illustrates the prosthetic heart valve in a compressed condition (e.g., when compressively retained within an outer catheter or sheath as described below). The prosthetic heart valve 10 includes a stent or stent frame 12 and a valve structure 14. A paravalvular leakage prevention wrap (not shown) can also be provided around the stent frame 12. The stent frame 12 can assume any of the forms mentioned above, and is generally constructed so as to be self-expandable or balloon-expandable from the compressed condition (FIG. 1B) to the normal, expanded condition (FIG. 1A). In some embodiments, the stent frame can be balloon expandable or expanded mechanically.

The valve structure 14 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 14 can be formed, for example, from bovine, porcine, equine, ovine and/or other suitable animal tissues. In some embodiments, the valve structure 14 can be formed, for example, from heart valve tissue, pericardium, and/or other suitable tissue. In some embodiments, the valve structure 14 can include or form one or more leaflets 16. For example, the valve structure 14 can be in the form of a tri-leaflet valve, a bi-leaflet valve, or another suitable valve. In some constructions, the valve structure 14 can comprise two or three leaflets that are fastened together at enlarged lateral end regions to form commissural joints, with the unattached edges forming coaptation edges of the valve structure 14. The leaflets 16 can be fastened to a skirt that in turn is attached to the frame 12. The upper ends of the commissure points can define an inflow portion 18 corresponding to a first or inflow end 20 of the prosthetic heart valve 10. The opposite end of the valve can define an outflow portion 22 corresponding to a second or outflow end 24 of the prosthetic heart valve 10. As shown, the stent frame 12 can have a lattice or cell-like structure, and optionally forms or provides crowns 26 and/or eyelets 28 (or other shapes) at the outflow and inflow ends 20, 24.

With the one exemplary construction of FIGS. 1A and 1B, the prosthetic heart valve 10 can be configured (e.g., sized and shaped) for replacing or repairing an aortic valve.

Alternatively, other shapes are also envisioned, adapted to mimic the specific anatomy of the valve to be repaired (e.g., stented prosthetic heart valves useful with the present disclosure can alternatively be shaped and/or sized for replacing a native mitral, pulmonic or tricuspid valve or compassionate use such as heterotopic implants).

Figure 2A:
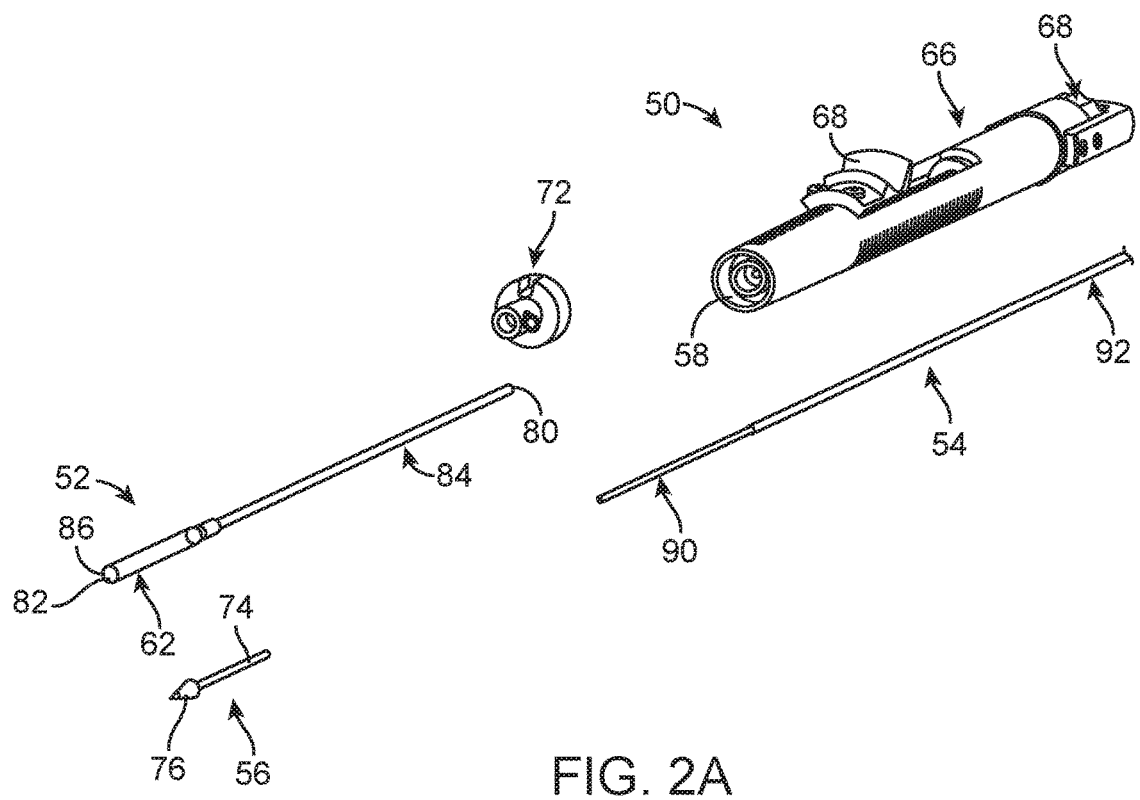
FIG. 2A is an exploded perspective view of a stented prosthetic heart valve delivery device in accordance with principles of the present disclosure.
Figure 2B:
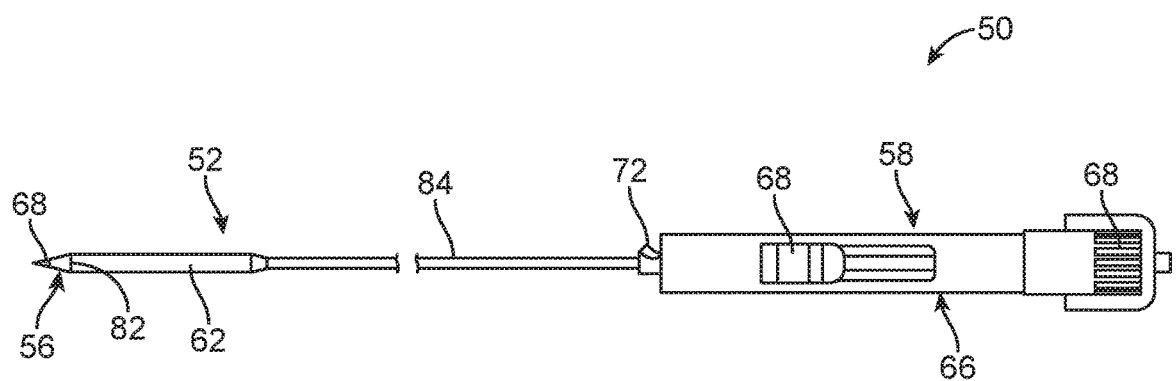
FIG. 2B is an assembled top view of the stented prosthetic heart valve delivery device of FIG. 2A.

With the above understanding of the stented prosthetic heart valves in mind, one embodiment of a delivery device 50 for percutaneously delivering the prosthesis or other implant is shown in simplified form in FIGS. 2A and 2B. The delivery device 50 includes a delivery sheath assembly 52, an inner shaft assembly 54, an inner shaft assembly 56 and a handle assembly 58. Details on the various components are provided below. In general terms, however, the delivery device 50 combines with a stented prosthetic heart valve (e.g., the prosthetic heart valve of FIGS. 1A-1B) to form a system for performing a therapeutic procedure on a defective heart valve of a patient. The delivery device 50 provides a loaded or delivery state in which a stented prosthetic heart valve is loaded over the inner shaft assembly 56 and is compressively retained within a capsule 62 of the delivery sheath assembly 52. The delivery sheath assembly 52 can be manipulated to withdraw the capsule 62 proximally from over the prosthetic heart valve via operation of the handle assembly 58, permitting the prosthetic heart valve to self-expand and partially release from the inner shaft assembly 56. When the capsule 62 is retracted proximally beyond the valve retainer 64, the stented prosthetic heart valve can completely release or deploy from the delivery device 50. The delivery device 50 can optionally include other components that assist or facilitate or control complete deployment, as desired.

Various features of the components 52-58 reflected in FIGS. 2A and 2B and as described below can be modified or replaced with differing structures and/or mechanisms. Thus, the present disclosure is in no way limited to the delivery sheath assembly 52, the inner shaft assembly 54, the shaft assembly 56 or the handle assembly 58 as shown and described below. Any construction that generally facilitates compressed loading of a stented prosthetic heart valve over an inner shaft via a retractable outer sheath or capsule is acceptable. Further, the delivery device 50 can optionally include additional components or features, such as a flush port assembly 72, a recapture sheath (not shown), etc.

In some embodiments, the delivery sheath assembly 52 defines proximal and distal ends 80, 82, and includes the capsule 62 and an outer shaft 84. The delivery sheath assembly 52 can be akin to a catheter, defining a lumen 86 (referenced generally) that extends from the distal end 82 through the capsule 62 and at least a portion of the outer shaft 84. The lumen 86 can be open at the proximal end 80 (e.g., the outer shaft 84 can be a tube). The capsule 62 extends distally from the outer shaft 84, and in some embodiments has a more stiffened construction (as compared to a stiffness of the outer shaft 84) that exhibits sufficient radial or circumferential rigidity to overtly resist the expected expansive forces of the stented prosthetic heart valve (not shown) when compressed within the capsule 62. For example, the outer shaft 84 can be a polymer tube embedded with a metal braiding, whereas the capsule 62 includes a laser-cut metal tube that is optionally embedded within a polymer covering. Alternatively, the capsule 62 and the out shaft 84 can have a more uniform or even homogenous construction (e.g., a continuous polymer tube). Regardless, the capsule 62 is constructed to compressively retain the stented prosthetic heart valve at a predetermined diameter when loaded within the capsule 62, and the outer shaft 84 serves to connect the capsule 62 with the handle assembly 58. The outer shaft 84 (as well as the capsule 62) is constructed to be sufficiently flexible for passage through a patient's vasculature, yet exhibits sufficient longitudinal rigidity to effectuate desired axial movement of the capsule 62. In other words, proximal retraction of the outer shaft 84 is directly transferred to the capsule 62 and causes a corresponding proximal retraction of the capsule 62. In other embodiments, the outer shaft 84 is further configured to transmit a rotational force or movement onto the capsule 62.

The inner shaft assembly 54 can have various constructions appropriate for supporting the delivery sheath assembly 52, including indirectly supporting the inner shaft assembly 56 (and a stented prosthetic heart valve disposed thereon) relative to the capsule 62. In some embodiments, the inner shaft assembly 54 includes an intermediate shaft or tube 90 and a proximal shaft or tube 92. The intermediate tube 90 is optionally formed of a flexible polymer material (e.g., PEEK), and is sized to be slidably received within the delivery sheath assembly 52. The intermediate tube 90 serves as a transition to the deflection assembly 60, and in some embodiments is a flexible polymer tubing (e.g., PEEK) having a diameter slightly less than that of the proximal tube 92. The proximal tube 92 can have a more rigid construction, configured for robust assembly with the handle assembly 58, such as a metal hypotube. Other constructions are also envisioned. For example, in other embodiments, the intermediate and proximal tubes 90, 92 are integrally formed as a single, homogenous tube or shaft. Regardless, the inner shaft assembly 54 forms or defines at least one lumen (not shown) sized, for example, to slidably receive a guide wire (not shown).

The shaft assembly 56 includes an inner support shaft 74 and a tip 76. The inner support shaft 74 is sized to be slidably received within the lumen 86 of the delivery sheath assembly 52, and is configured for mounting to the deflection assembly 60. The inner support shaft 74 can be a flexible polymer tube embedded with a metal braid. Other constructions are also acceptable so long as the inner support shaft 74 exhibits sufficient structural integrity to support a loaded, compressed stented prosthetic heart valve (not shown). The tip 76 forms or defines a nose cone having a distally tapering outer surface adapted to promote atraumatic contact with bodily tissue. The tip 76 can be fixed or slidable relative to the inner support shaft 74. The shaft assembly 56 can define a continuous lumen (not shown) sized to slidably receive an auxiliary component such as a guide wire (not shown).

The handle assembly 58 generally includes a housing 66 and one or more actuator mechanisms 68 (referenced generally). The housing 66 maintains the actuator mechanism(s) 68, with the handle assembly 58 configured to facilitate sliding movement of the delivery sheath assembly 52 relative to other components (e.g., the inner shaft assembly 54, the shaft assembly 56). The housing 66 can have any shape or size appropriate for convenient handling by a user.

With the above general explanations of exemplary embodiments of the components 52-58 in mind, the present disclosure provides many packaging embodiments for storing prosthetic heart valves in a "dry" (without excess glutaraldehyde) state either with or without part of a delivery device (e.g., the shaft assembly 56 of the delivery device 50). The disclosed embodiments are configured to allow for sterilization of a prosthetic heart valve within the packaging and also to maintain the air humidity level within the packaging. In the embodiments disclosed herein, the prosthetic heart valves can either be stored in either the expanded or compressed condition.

Figure 3:
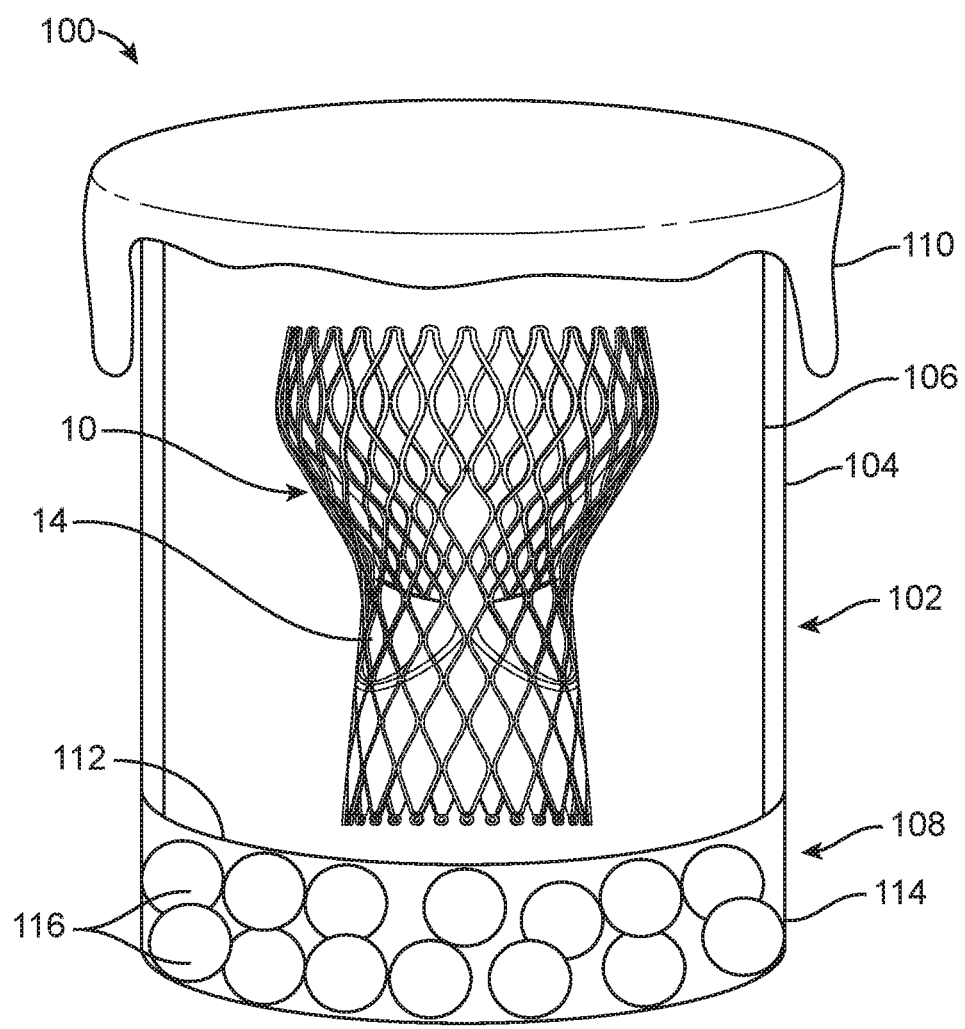
FIG. 3 is a schematic illustration of packaging for the prosthetic heart valve.

One embodiment of container for dry valve packaging 100 for a prosthetic heart valve or other implant (e.g., the prosthetic heart valve 30) is schematically depicted in FIG. 3. In this embodiment, the prosthetic heart valve 30 can be housed within a container 102 made of a non-permeable material including a first compartment 104 having two open ends 106, 108. The container 102 can optionally be formed with a double wall to reduce the risk of condensation buildup that can result from temperature variations during shipping. Examples of non-permeable materials that can be used with all embodiments disclosed include glass, metal and plastic/rubber polymers. Secured over one end 106 is a cover 110. In some embodiments, the cover 110 is made of a material that has a high ingress protection (IP) rating and is otherwise configured to prevent moisture within the container 102 from escaping at the end 106. Examples of suitable materials that can be used in all embodiments disclosed herein include Tyvek® (flashspun high-density polyethylene fibers), medical grade paper, plastic polymer or the like to further allow for "dry" sterilization techniques including gas-based or radiation-based sterilization techniques (e.g., EtO or hydrogen peroxide sterilization). The second end 108 is covered by a semi-permeable membrane 112 that divides the first compartment 104 from a second compartment 114. The semi-permeable membrane 112 is permeable to gas and/or moisture. Within the second compartment 114 is hydrogel 116 (e.g., polyacrylamide, sodium polyacrylate or the like) in the form of beads, gel pad or a sheet, for example. The hydrogel 116 regulates the humidity within the container 102 through the equilibration between humidity within the container 102 and the hydrogel's 116 ability to hold and release water. In other words, water molecules are either released or absorbed by the hydrogel through a diffusion-driven mechanism, if a gradient of humidity between the inside and the outside of the hydrogel exists. Humidity regulation is important to prevent the tissue of the valve structure 14 from drying out. When the partially-hydrated hydrogel 116 is present within the second compartment 114, which is saturated with air of a predefined humidity, the water molecules from the air will be absorbed by the hydrogel 116 if the air humidity is high (i.e. when the thermodynamics favor hydrogel hydration).

For all of the embodiments disclosed herein, the hydrogel 116 can be preloaded, via soaking or the like, with glycerol or other hygroscopic substance. Glycerol and other hygroscopic substances release moisture and, when used in combination with the hydrogel 116, maintain a sufficient amount of moisture to the valve structure 14 when housed in the container 102. The disclosed embodiments are configured to create a greenhouse-like atmosphere within the container 102 where the glycerol, once released from the hydrogel 116, will collect on the inner walls of the container 102 rather than completely drying off of the valve structure 14. The end result is an atmospheric condition inside the container 102 that is high in glycerol, reducing the drying of the valve structure 14 during the sterilization process and while the packaging 100 is being stored prior to use (i.e. a shelf life of the packaging 100 is increased with the use of glycerol or the like).

Figure 4:
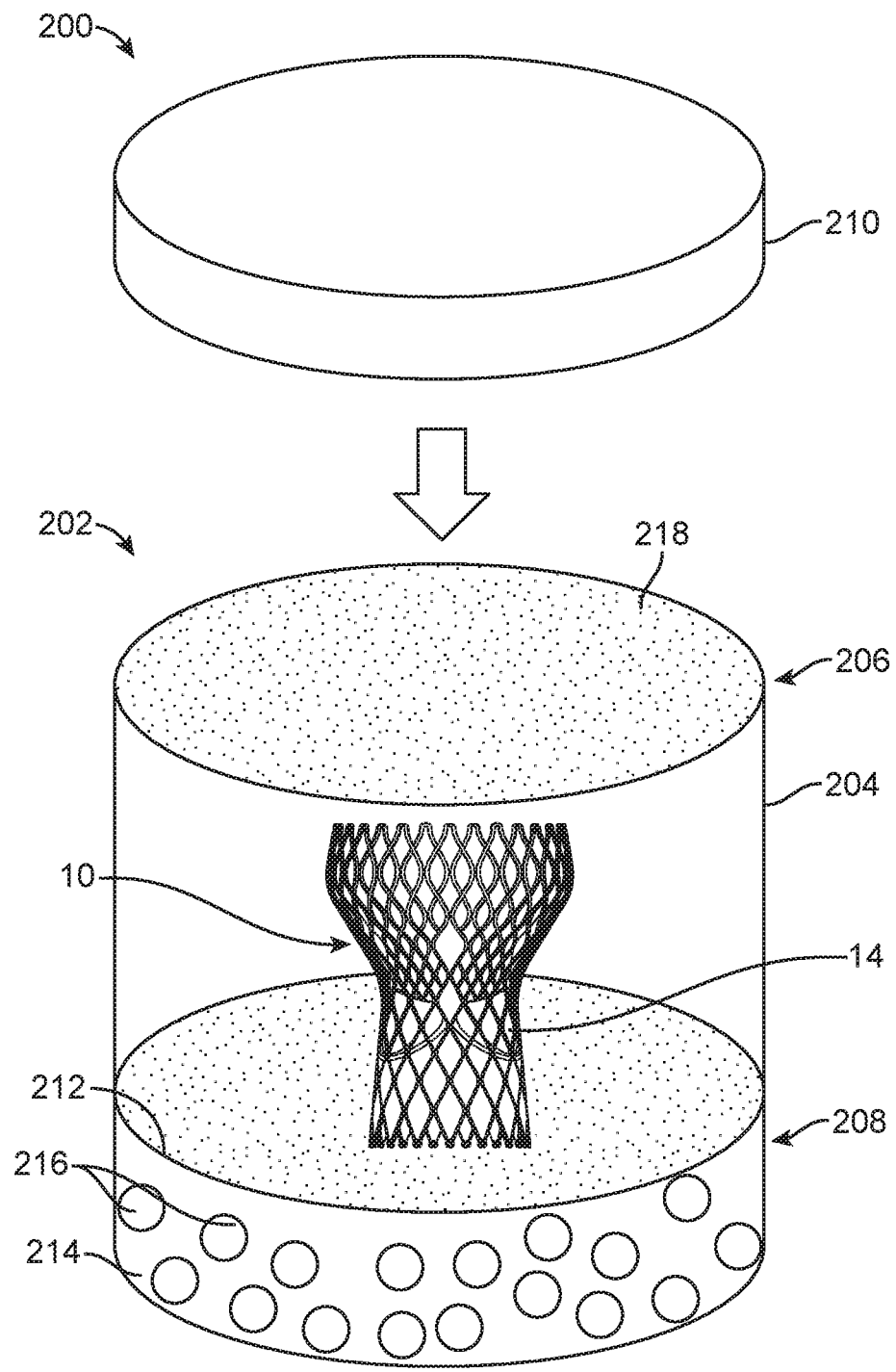
FIG. 4 is a schematic illustration of an alternate packaging for the prosthetic heart valve.

A similar packaging 200 embodiment is illustrated in FIG. 4. In this embodiment, the prosthetic heart valve 30 is housed within a container 202 made from a non-permeable material including a first compartment 204 having two open ends 206, 208. Secured over one end 206 is a gas permeable membrane 218 over which a lid 210 can be positioned. The lid 210 can be screwed on or otherwise removably secured. Similar to the prior embodiment, the second end 208 of the container 202 is covered by a semi-permeable membrane 212 that divides the first compartment 204 from a second compartment 214. The semi-permeable membrane 212 is permeable to gas and/or moisture. Within the second compartment 214 is hydrogel 216, of the type described above. As with the prior disclosed embodiment, the hydrogel 216 regulates the humidity within the container 202 through the equilibration between humidity within the container 202 and the hydrogel's 216 ability to hold water.

Figure 5:
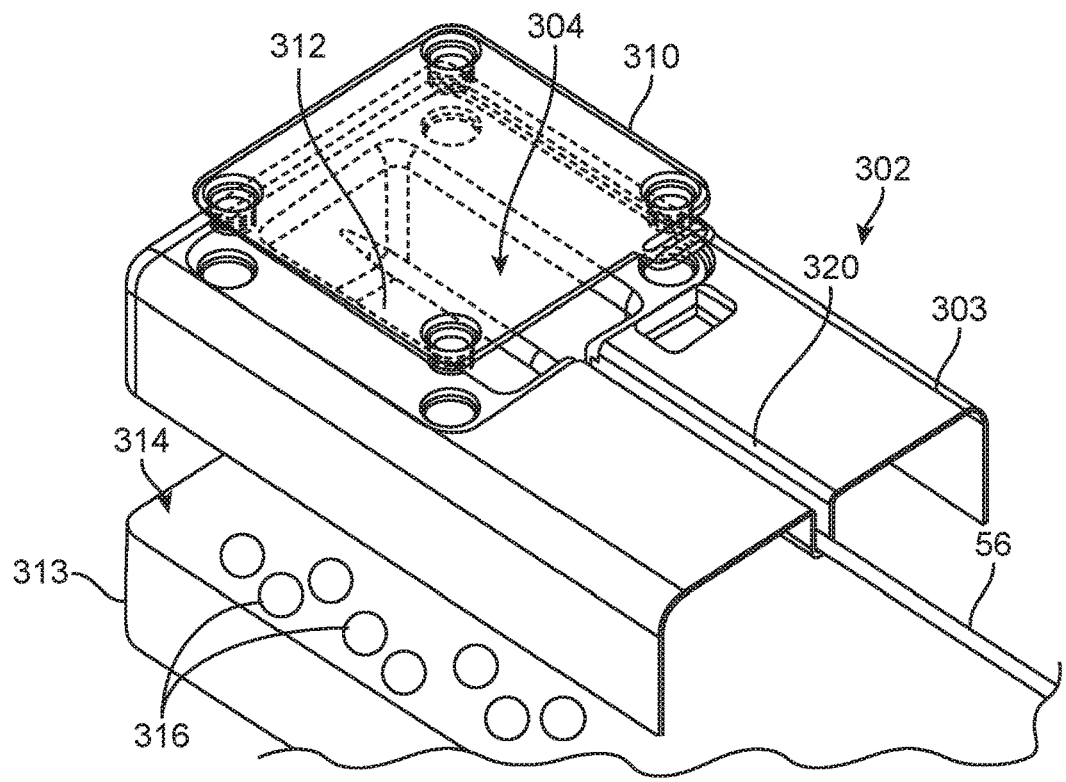
FIG. 5 is a perspective illustration of packaging for the prosthetic heart valve (not shown) and a portion of the delivery device.

In some embodiments, the prosthetic heart valve 30 is packaged with at least a portion of the delivery device, such as the shaft assembly 56. For example, in the embodiment of FIG. 5, the prosthetic heart valve or other implant (not shown for ease of illustration) can be packaged within a container 302 along with the shaft assembly 56. The container 302 can be made of any non-permeable material, such as one of those disclosed above, for example. As shown, the container 302 includes first and second portions 303, 313. The first portion 303 defines a first compartment 304 and a channel 320 in which a portion of a delivery device can be positioned (e.g., the shaft assembly 56). The first compartment 304 is also sized so that the prosthetic heart valve or other implant can be loaded onto the shaft assembly 56 and secured within the first compartment 304. In some embodiments, the first compartment 304 will include a removable, non-permeable cover 310. Further, the first compartment 304 includes a semi-permeable membrane 312 so that gas and/or moisture can move through the semi-permeable membrane 312 between the two portions 303, 313. The second portion 313 an area 314 in which hydrogel 316 can be positioned and optionally contained with a membrane or the like. Alternatively or in addition, hydrogel can be positioned within the first compartment 304. The hydrogel 316 can be any of the type disclosed herein and functions in a similar manner to maintain a desired humidity level within the container 302.

Figure 6:
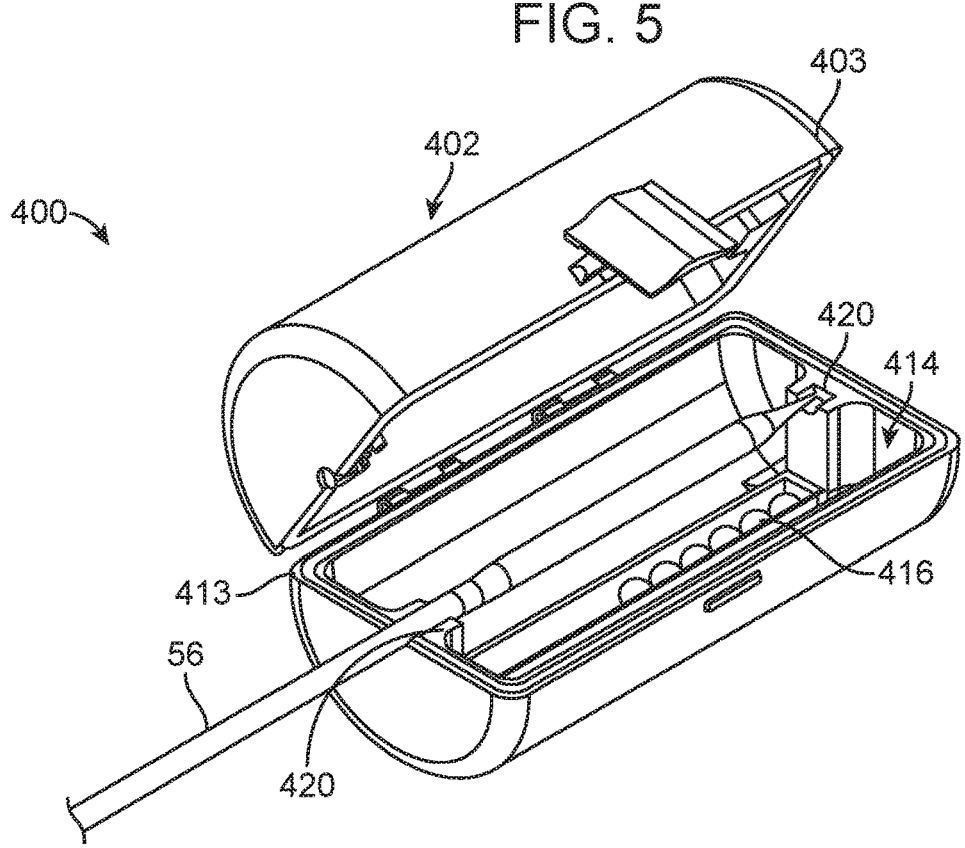
FIG. 6 is a perspective illustration of packaging for the prosthetic heart valve (not shown) and the portion of the delivery device.

Referring now also to FIG. 6, which illustrates an alternate packaging 400 for a prosthetic heart valve (not shown; e.g., the prosthetic heart valve 30) and at least a portion of a delivery device, such as the shaft assembly 56. In this embodiment, the packaging 400 includes a container 402 that is made of a non-permeable material, which includes first and second portions 403, 413 that hingedly connected and shown in an open configuration in FIG. 6. The container 402 can be made of any non-permeable material, such as one of those disclosed above, for example. The second portion 413 includes supports 420 for receiving the shaft assembly 56, which can include a prosthetic heart valve or other implant (e.g., the prosthetic heart valve 30) loaded thereto. Similar to prior disclosed embodiments, the second portion 413 defines a compartment 414 in which hydrogel 416 can be positioned. The hydrogel 416 can be contained within a semi-permeable membrane 412 so that gas and/or moisture can move through the semi-permeable membrane while the hydrogel 416 is contained. The hydrogel 416 can be any of the type disclosed herein and functions in a similar manner to maintain a desired humidity level for air within the container 402 when the container 402 is closed. The container 402 can optionally further include a vent (not visible, see also FIG. 8B and related disclosure) that has a high IP rating to retain moisture within the container 402 but is suitable for gas-based or radiation-based sterilization techniques.

Figure 7:
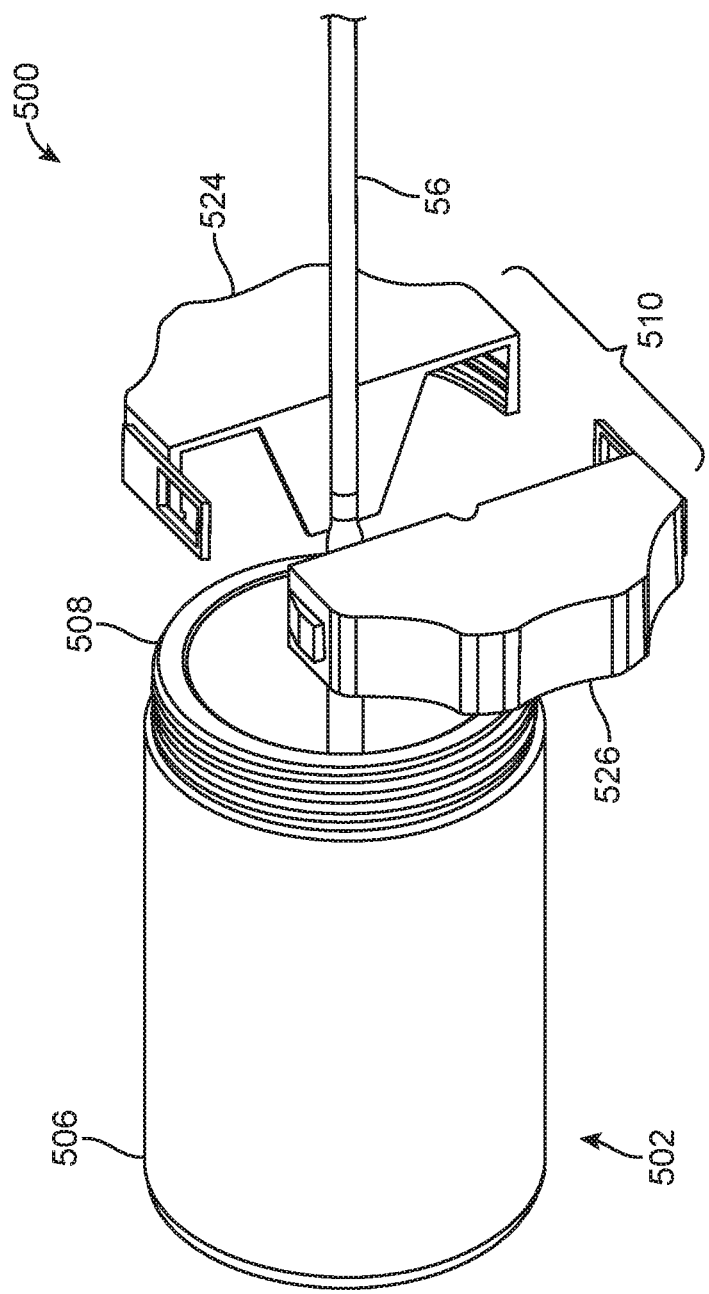
FIG. 7 is a perspective illustration of packaging for the prosthetic heart valve (not shown) and the portion of the delivery device.

Referring now also to FIG. 7, which illustrates an alternate packaging 500 for the prosthetic heart valve (not visible) and at least a portion of a delivery device, such as the shaft assembly 56. This embodiment is largely similar to those disclosed above in that the packaging 500 includes a container 502 that can house a prosthetic heart valve or other implant (e.g., the prosthetic heart valve 30) loaded onto the delivery device (e.g., the shaft assembly 56). The container 502 can be made of a non-permeable material, such as one of those disclosed above, for example. The container 502 includes two ends 506, 508 and can optionally further include a vent (not visible, see also FIG. 8B and related disclosure) at one end 506 that has a high IP rating to retain moisture within the container 502 but is suitable for gas-based or radiation-based sterilization techniques. A cover 510 is positioned over a second end of container 502, over the shaft assembly 56. The cover 510 can include two interlocking pieces 524, 526, arranged and configured to snap over the shaft assembly 56 and screw on to the second end 508 of the container 502, for example, to generally seal in air and moisture within the container 502. The container 502 can also include a compartment (not visible) for the placement of hydrogel, in any of the ways described with respect to other embodiments, for the same purpose of regulating humidity within the container 502.

Figure 8A:
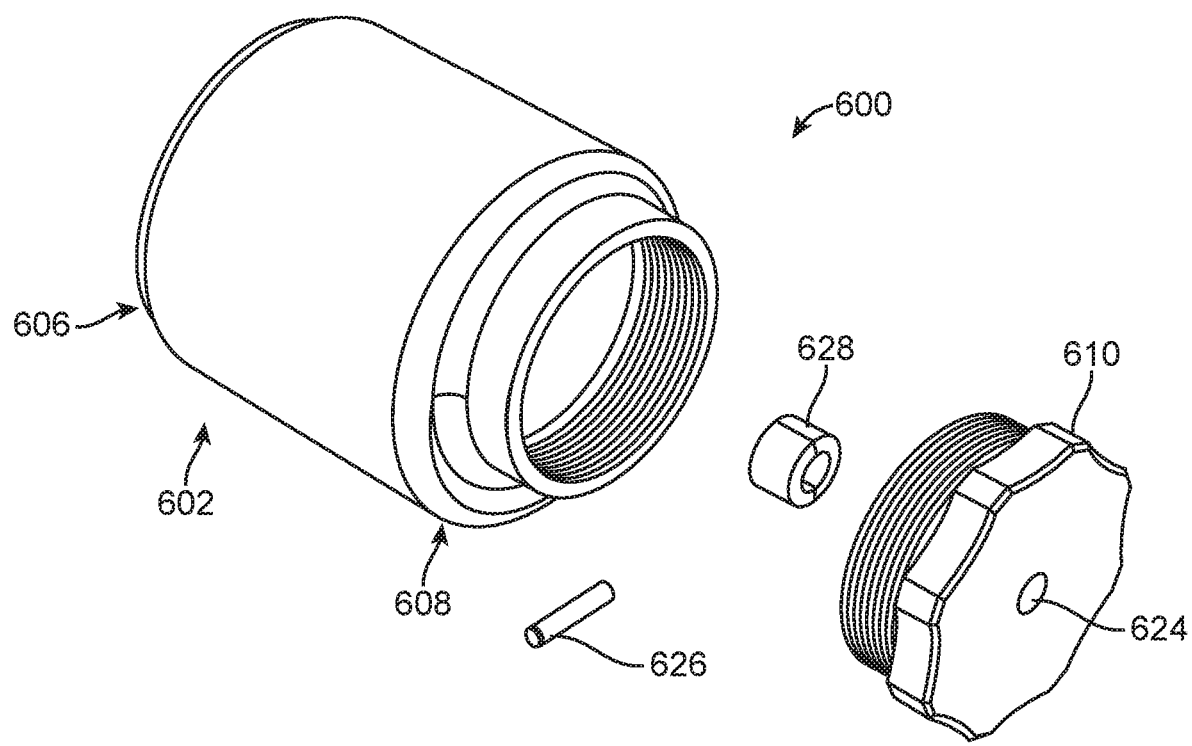
FIGS. 8A-8B are perspective illustrations of packaging for the prosthetic heart valve and the portion of the delivery device (the prosthetic heart valve and delivery device are not shown).
Figure 8B:
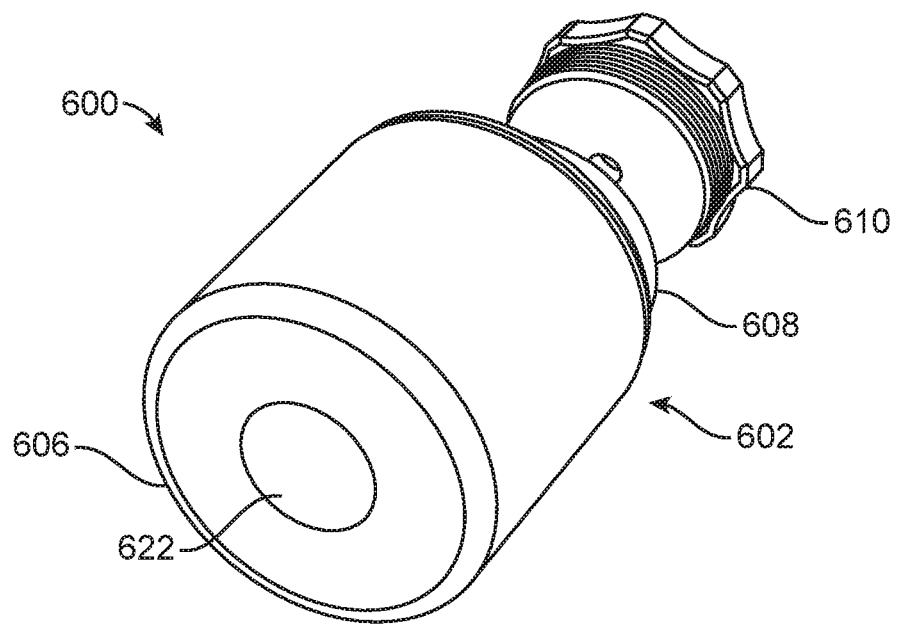

Turning now also to FIGS. 8A-8B, which illustrate an alternate packaging 600 for the prosthetic heart valve or other implant (not shown; e.g., the prosthetic heart valve 30) and at least a portion of the delivery device (also not shown). This embodiment is largely similar to those disclosed above in that the packaging 600 includes a container 602 made of a non-permeable material, such as one of those disclosed above, that can house a prosthetic heart valve loaded onto a delivery device (e.g., the prosthetic heart valve 30 and the shaft assembly 56). The container 602 can optionally include a vent 622 at one end 606 that has a high IP rating to retain moisture within the container 602 but is suitable for gas-based or radiation-based sterilization techniques (e.g., Tyvek®) or the like. A cover 610 is positioned at a second end 608 of the container 602, over the shaft assembly 56. The cover 610 can be arranged and configured to screw on to the second end 608, for example, to generally seal in air and retain moisture within the container 602. The cover 610 further includes an aperture 624, a sealing pin 626, a seal 628 configured to interface between the delivery device and the cover 610. The sealing pin 626 can be positioned within the aperture 624 to put pressure on the seal 628, which correspondingly grips a portion of the delivery device positioned within the seal 628. The seal 628 can be made of silicone, for example. The container 602 can also include a compartment (not visible) for the placement of hydrogel, in any of the ways described with other embodiments for the same purpose of regulating humidity within the container 602.

Figure 9A:
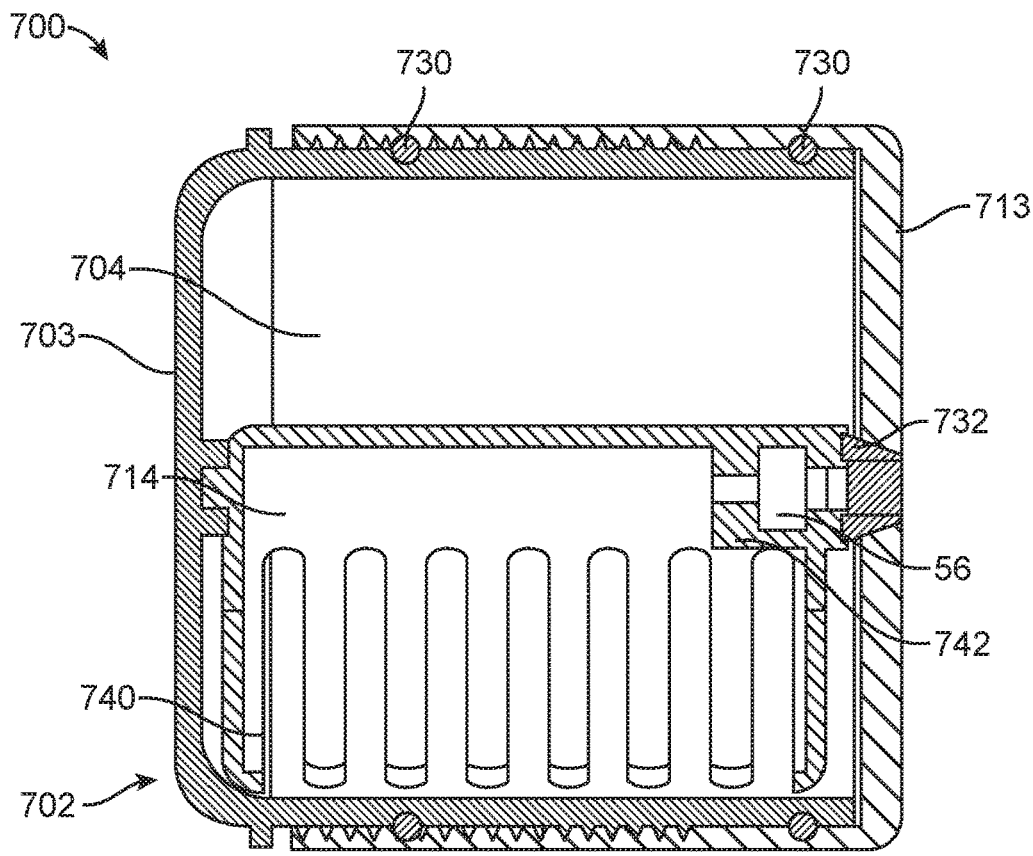
FIG. 9A is a cross-sectional view of packaging for the prosthetic heart valve and the portion of the delivery device.
Figure 9B:
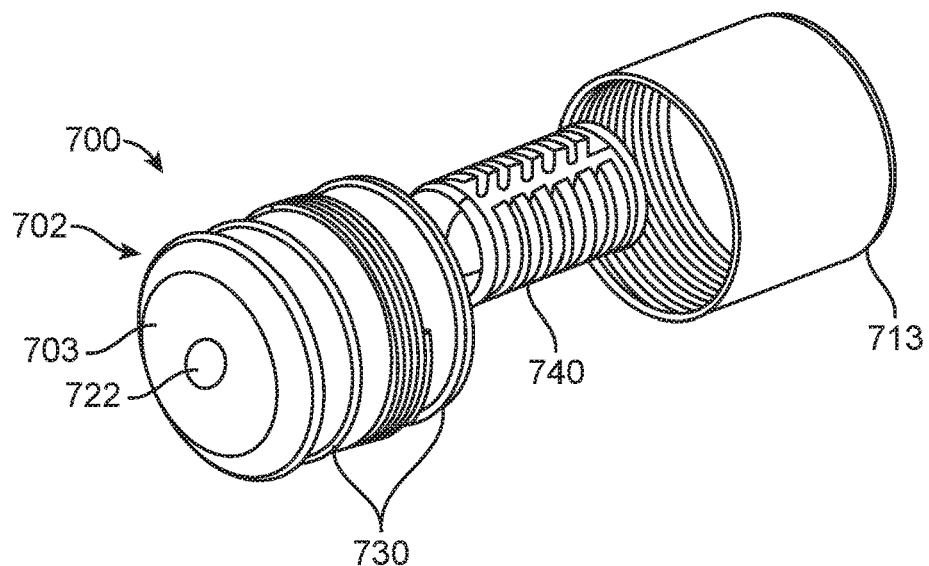
FIG. 9B is a partially-exploded perspective view of the packaging of FIG. 9A.

Referring now also to FIGS. 9A-9B, which illustrate yet another packaging 700 for dry packing a prosthetic heart valve or other implant and a shaft assembly of a delivery device (the prosthetic heart valve and delivery device are not shown for ease of illustration; see, e.g., the prosthetic heart valve 30 and the shaft assembly 56 of FIGS. 1A-1B). In this embodiment, the packaging 700 includes a container 702 having two portions 703, 713 that can be screwed or otherwise removably connected together. The container 702 further includes first and second halves 704, 714 and is made of a non-permeable material, such as one of those disclosed above, for example. The two portions 703, 713 of the container 702 can be sealed with provided seals (e.g., o-rings) 730, for example, that retain moisture within the container 702. In addition, the first half 704 is connected to a seal 732 through which the shaft assembly 56 of the delivery system 50 can be secured (see also FIGS. 2A-2B).

The packaging 700 also includes a hinged cage 740 for positioning around protecting the prosthetic heart valve within the container 702. In some embodiments, the cage 740 is configured to be positioned within only the second half 714 of the container 702 or is otherwise offset within the container 702. The cage 740 can be offset with respect to the container 702 so that the prosthetic valve can be compressed and expanded out of line with a central axis of the portion of the delivery device (e.g., the shaft assembly 56), which can make loading and attachment of the prosthetic valve to the delivery device easier. As with prior disclosed embodiments, the container 702 may further house hydrogel (not shown) of any of the types and forms disclosed herein. For example, hydrogel can be housed in the first half 704, for regulating humidity within the container 702. Optionally, the container 702 can additionally include a window or vent 722 to allow for gas-based or radiation-based sterilization techniques or the like, as discussed above with respect to prior embodiments.

One example method of assembling the packaging 700 of FIGS. 9A-9B can be accomplished as follows. First, the conical seal 732 and first portion 703 of the container 702 are secured to a portion of a delivery device (e.g., the shaft assembly 56) so that the portion of the delivery device extends through the conical seal 732. Then, the cage 740 is snapped around the prosthetic heart valve, ensuring that a proximal portion 742 of the cage 740 is snapped around the shaft assembly 56 and the prosthetic valve sits within the cage 740. The seal 732 and the first portion 703 of the container 700 are brought back to the cage 740. A bottom of the cage 740 has a locating pin 744, which can be used with assembling the cage 740 into the second portion 713. Then, the first and second portions 703, 713 of the container 702 are screwed together or otherwise connected until there is a firm seal between the conical seal 732 and the first half 704 of the container 702. The container 702 is then assembled onto an end of the shaft assembly 56 and attached to the second portion 713, aligning concentrically with the shaft assembly 56.

In other embodiments, the second portion 713 is assembled over the shaft assembly 56 and the prosthetic valve is attached to shaft assembly 56. Then, the cage 740 is closed around prosthetic valve, so that the prosthetic valve sits inside the cage 740. Then, the rest of the container 702 is assembled onto the shaft assembly 56 and attached to the second portion 713, aligning concentrically with shaft assembly 56. The disclosure is not intended to be limited to any particular method of assembly.

Figure 10A:
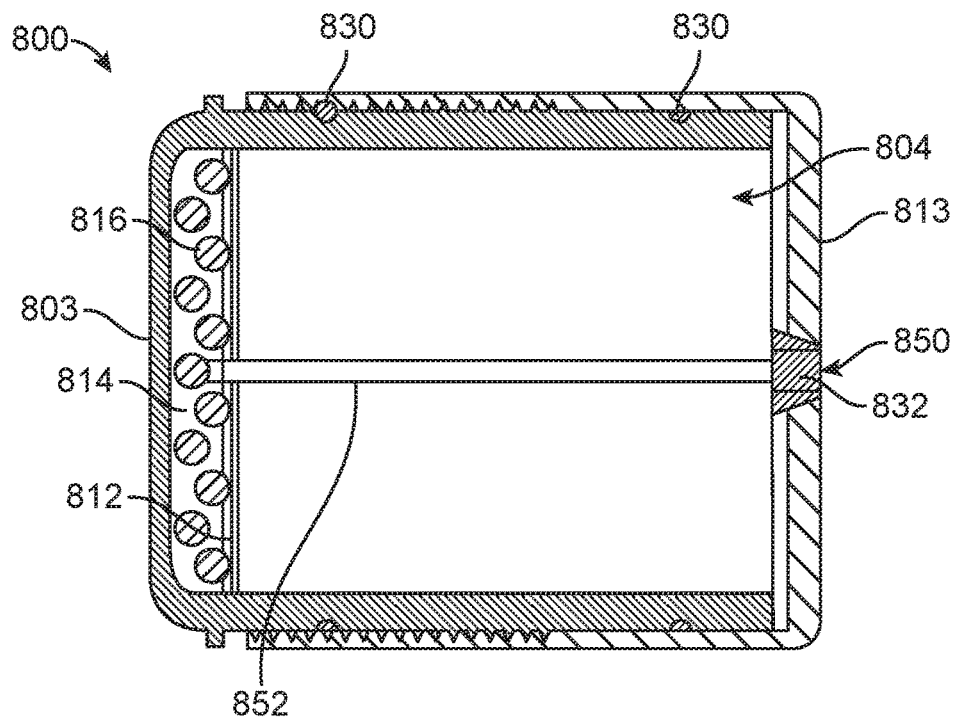
FIG. 10A is a cross-sectional view of packaging for the prosthetic heart valve and the portion of the delivery device.
Figure 10B:
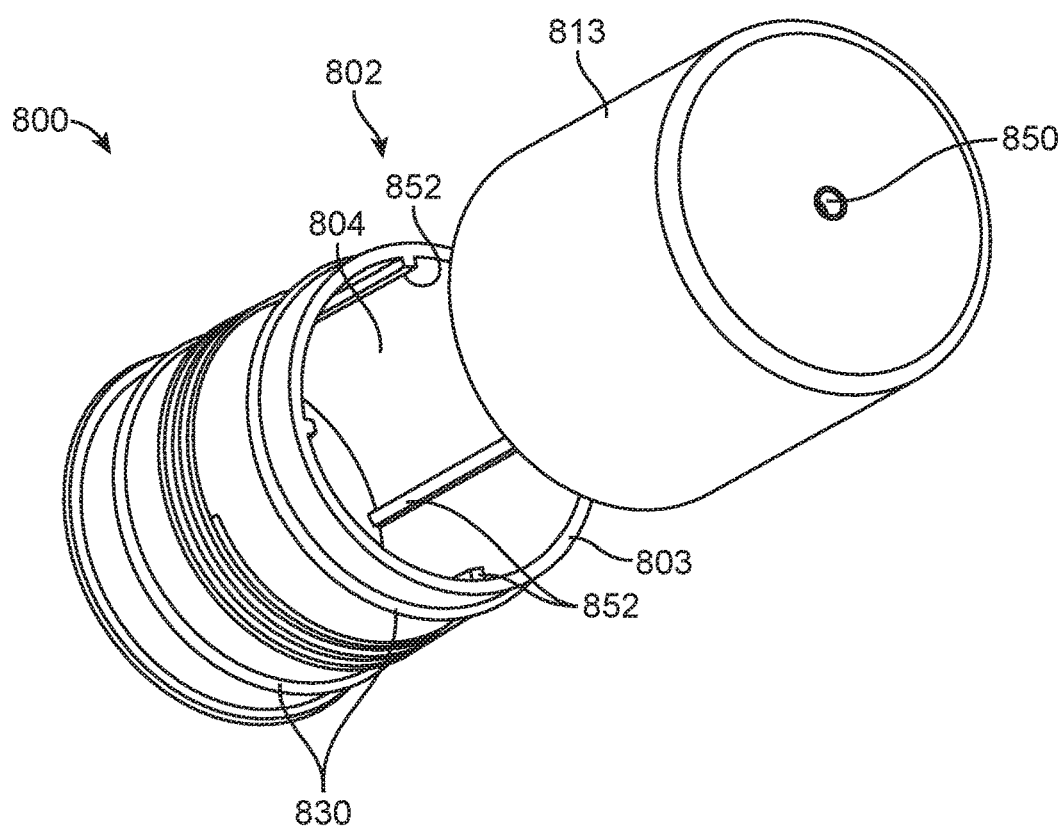
FIG. 10B is a partially-exploded perspective view of the packaging of FIG. 10A.

Referring in addition to FIGS. 10A-10B, which illustrate another dry packaging 800 for packing a prosthetic heart valve or other implant and a shaft assembly of a delivery device (the prosthetic heart valve and delivery device are not shown for ease of illustration; see also, for example, FIGS. 1A-2B and related disclosure). In this embodiment, the packaging 800 includes a container 802 having two portions 803, 813 that can be screwed or otherwise removably connected together. The container 802 can be made of a non-permeable material, such as any one of those disclosed above, for example. The two portions 803, 813 of the container 802 can be sealed with provided seals (e.g., o-rings 830), for example. The container 802 further includes an aperture 850 having a seal 832 through which the shaft assembly 56 of the delivery device 50 can be secured (see also, FIGS. 2A-2B). As with prior disclosed embodiments, the container 802 may further house the prosthetic heart valve in a compartment 814 and may house hydrogel 816 in another compartment 804, which is divided from the first compartment by a semi-permeable membrane or lid 812. The semi-permeable membrane 812 and hydrogel 816 can be of any of the types and forms disclosed herein. Guide rails 852 (a select few of which are referenced) can also be provided to position and lock the semi-permeable membrane or lid 812 in place. More or fewer guide rails 852 can be provided. As with prior disclosed embodiments, the hydrogel 816 is provided to regulate humidity within the container 802. Optionally, the container 802 can further include a window or vent (not visible) to allow for gas-based or radiation-based sterilization techniques, as discussed above with respect to prior embodiments.

Figure 11:
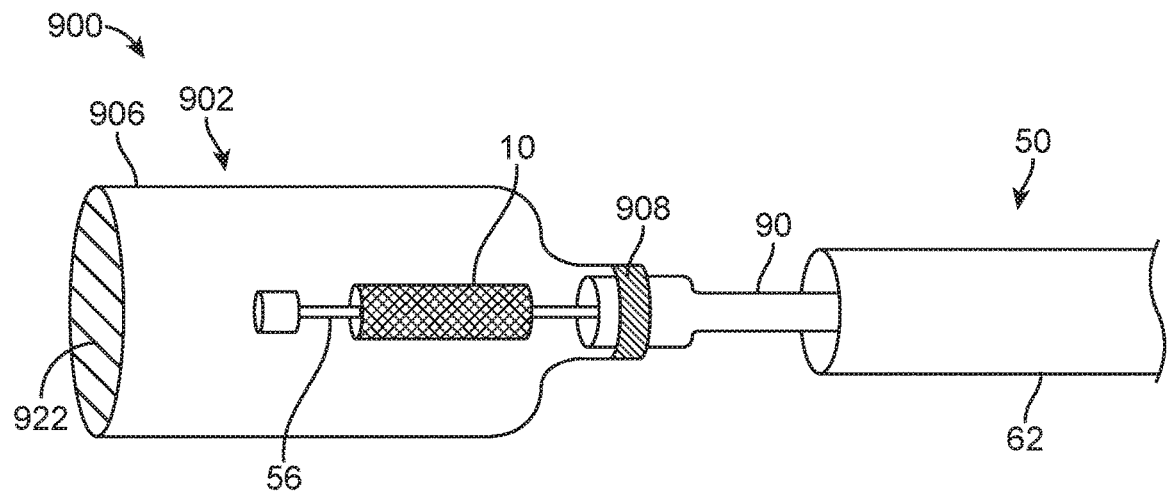
FIG. 11 is a schematic illustration of packaging for the prosthetic heart valve and the portion of the delivery device.

Yet another packaging 900 for dry packing the prosthetic heart valve 30 loaded onto the shaft assembly 56 of a delivery device 50 is shown in FIG. 11. In this embodiment, the packaging 900 includes a container 902 for housing the prosthetic heart valve 30 or other implant. The container 902 has two open ends 906, 908. The container 902 can be made of a non-permeable material, such as one of those disclosed above, for example. Secured over one end 906 is a cover 922 having a high IP rating as discussed with respect to prior embodiments. The second end 908 of the container 902 is arranged to be sealably connected over a portion of the delivery device 50 (e.g., the shaft assembly 56). In one embodiment, the second end 908 and delivery device 50 are configured to be threadably connected.

Figure 12:
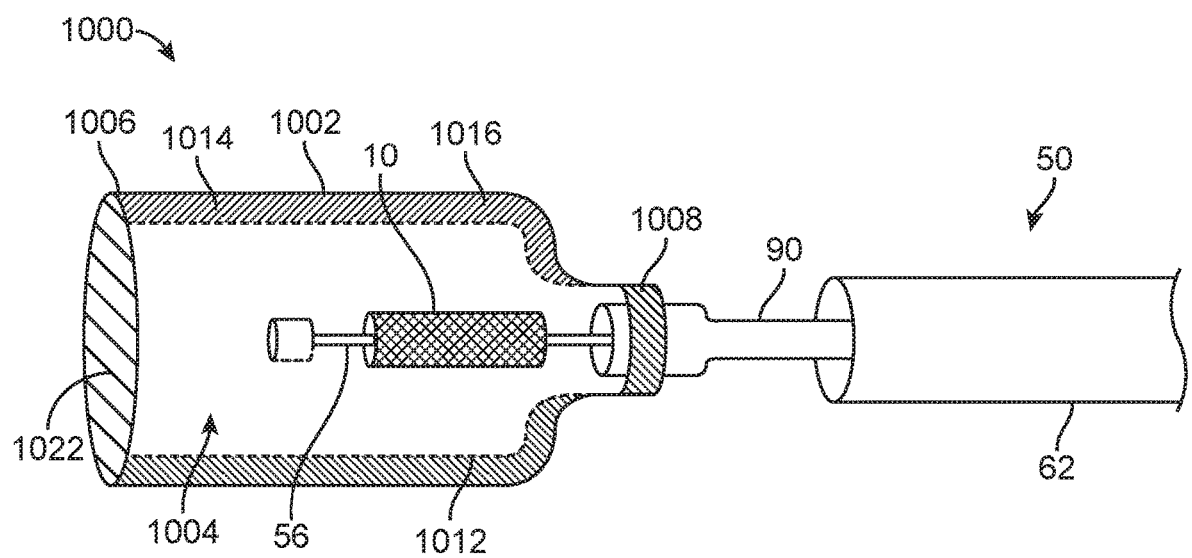
FIG. 12 is a schematic illustration of packaging for the prosthetic heart valve and the portion of the delivery device.

Turning now also to FIG. 12, which illustrates another embodiment. In this embodiment, the packaging 1000 includes a container 1002 for housing the prosthetic heart valve 30. The container 1002 has two open ends 1006, 1008. The container 1002 can be made of a non-permeable material, such as one of those disclosed above, for example. Secured over one end 1006 is a cover 1022 having a high IP rating as discussed with respect to prior embodiments. The second end 1008 of the container 1002 is arranged to be sealably connected over a portion of the delivery device 50 (e.g., shaft assembly 56). This embodiment is similar to the prior embodiment of FIG. 11 in that the second end 1008 can be configured to be threaded onto the delivery device 50. In addition, the container 1002 includes a first compartment 1004 for housing the prosthetic heart valve 30 and a second compartment 1014 for housing hydrogel 1016. An outer wall of the container 1002 is made of an impermeable material and an inner wall 1012 separating the first and second compartments 1004, 1014 is made of a semi-permeable material that allows air and/or moisture to pass through between the compartments 1004, 1014. Hydrogel 1016 (e.g., polyacrylamide, sodium polyacrylate or the like) is positioned within the second compartment 1014 in the form of beads, gel pad or a sheet, for example. As with prior embodiments, the hydrogel 1016 regulates the humidity within the container 1002 through the equilibration between humidity within the container 1002 and the hydrogel's 1016 ability to hold water. In embodiments where glycerol or the like is provided within the container 1002, separate from the valve structure, to reduce drying of tissue of the valve structure, glycerol could be pre-coated to an interior of the container 1002 in a gel bead or liquid format, for example. The hydrogel 1016 can also be loaded with glycerol or the like to keep the tissue of the valve structure moist for a period of time while stored within the container 1002. In addition, the inner wall 1012 of the container 1002 can be vented or slotted to allow proximity between the glycerol on the container 1002 and the already glycerol coated prosthetic heart valve 30.

Figure 13A:
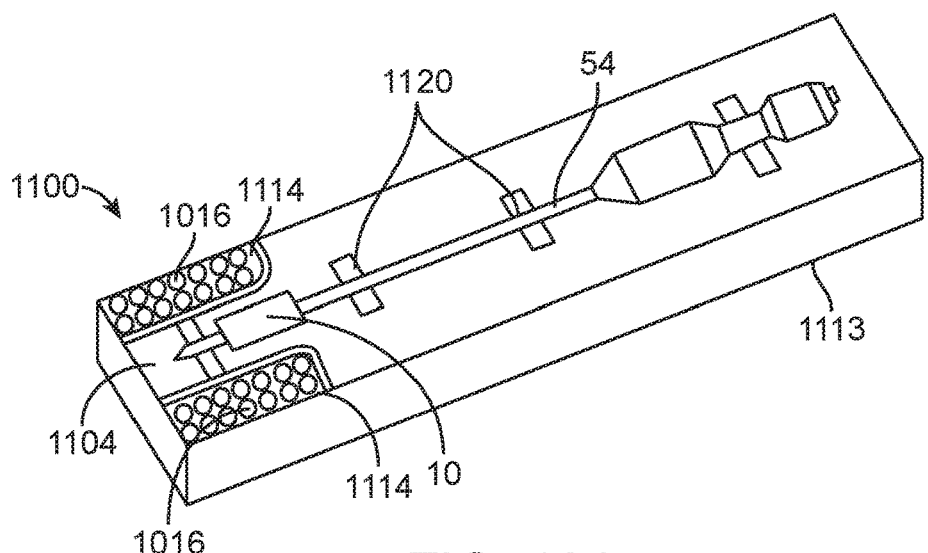
FIG. 13A is a schematic perspective view of packaging for the prosthetic heart valve and the portion of the delivery device.
Figure 13B:
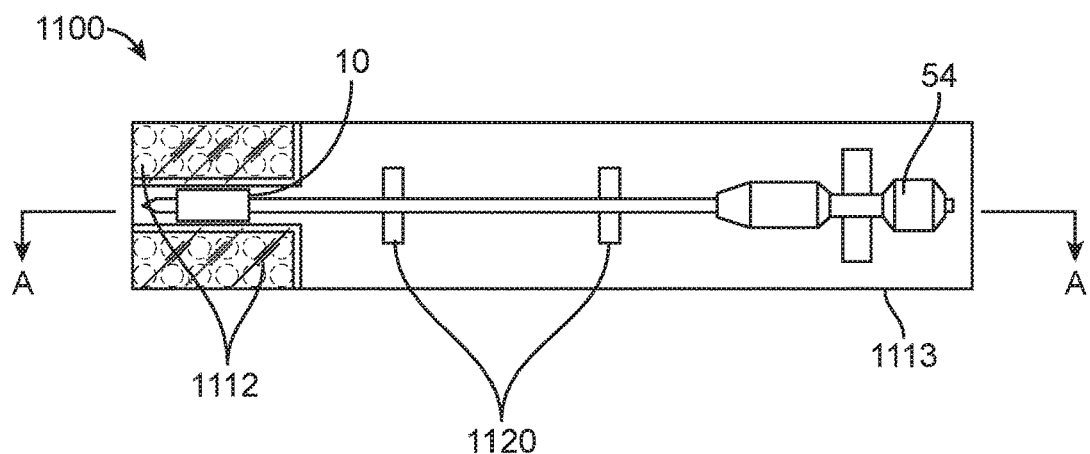
FIG. 13B is a schematic top view of the packaging of FIG. 13A.
Figure 13C:
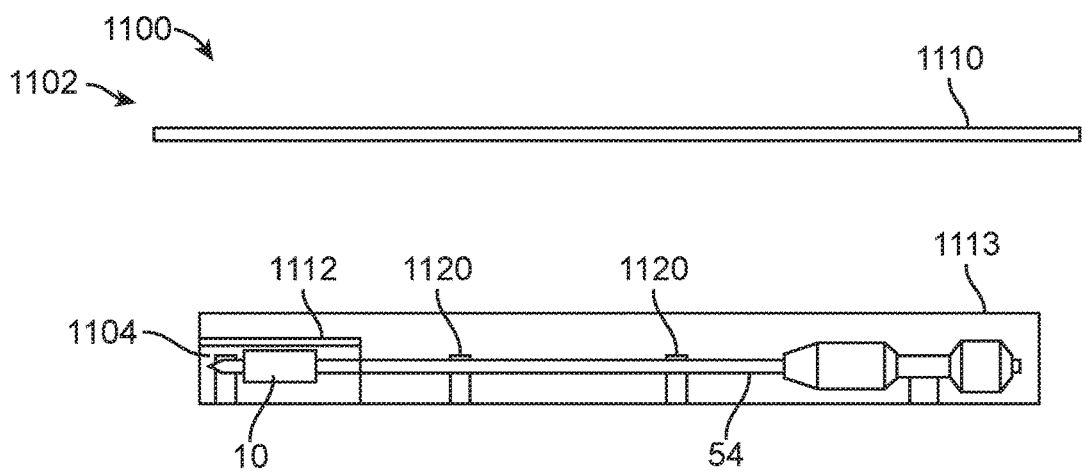
FIG. 13C is a schematic, cross-sectional view of the packaging of FIGS. 13A-13B as viewed along line A-A.

Referring now also to FIGS. 13A-13C that illustrate an alternate packaging 1100 for the prosthetic heart valve 30 or other implant and at least a portion of the delivery device, such as the shaft assembly 56. In this embodiment, the packaging 1100 includes a container 1102 that is made of a non-permeable material, which includes a portion or tray 1113 over which a cover 1110 can be positioned (the cover is only illustrated in FIG. 13C for ease of illustration). The cover 1110 can be positioned over the tray 1113 to create a barrier between the inside of the container 1002 and the exterior environment. Suitable materials for the cover 1110 include, but are not limited to Tyvek® (flashspun high-density polyethylene fibers) or the like. The container 1102 can be made of any non-permeable material, such as one of those disclosed above, for example. The second portion 1113 includes supports or clips 1120 for receiving and maintaining at least a portion of the inner shaft assembly 54, which can include the prosthetic heart valve 30 loaded thereto and is positioned in a first compartment 1104. Similar to prior disclosed embodiments, the second portion 1113 defines one or more compartments 1114 in which hydrogel 1116 can be stored. The hydrogel 1116 can be contained within a semi-permeable membrane 1112 so that gas and/or moisture can move through the semi-permeable membrane. The hydrogel 1116 can be any of the type disclosed herein and functions in a similar manner to maintain a desired humidity level for air within the container 1102 when the container 1102 is closed (i.e. when the first portion 1103 is positioned over the second portion 1113).

Figure 14A:
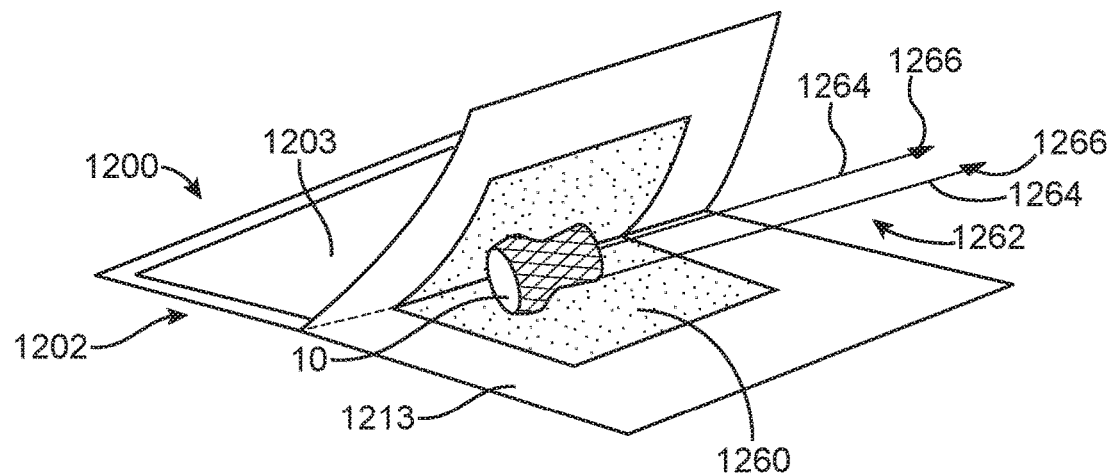
FIG. 14A is a schematic illustration of packaging for the prosthetic heart valve prior to the prosthetic heart valve being sealed within a container of the packaging.
Figure 14B:
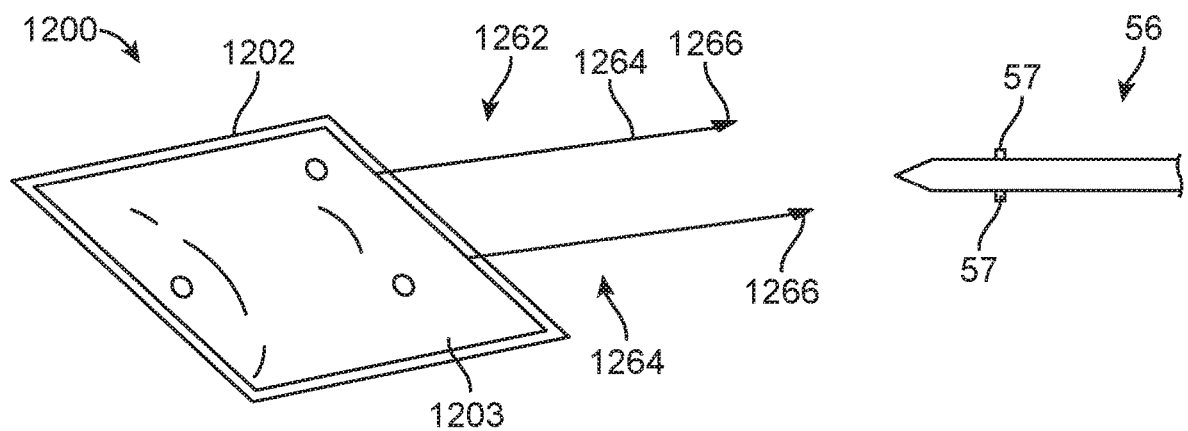
FIG. 14B is a schematic illustration of the packaging of FIG. 14A after the prosthetic heart valve is sealed within the container; also showing a quick connect system for attachment to the delivery device.

Referring now also to FIGS. 14A-14B, which illustrate an alternate packaging 1200 for the prosthetic heart valve 30 or other implant. In this embodiment, the packaging 1200 includes a container 1202 including two portions 1203, 1213 or sheets of flexible non-porous material, such as aluminum, for example, in which the prosthetic heart valve 30 or other implant can be housed. The container 1202 can further include a pad or cushion 1260 to protect the prosthetic heart valve 30 from exterior mechanical forces. The pad 1260 can optionally be soaked with glycerol or the like to help regulate moisture within the container 1202 when the two portions 1203, 1213 are sealed together to form a pouch around the prosthetic heart valve 30, as is shown in FIG. 14B. The packaging 1200 can further include a quick connect system 1262 around which the two portions 1203, 1213 are sealed. The quick connect system 1262 includes tether cables 1264 secured to the prosthetic heart valve 30 and extending outside of the container 1202. The tether cables 1264 can include fasteners 1266 to be connected to corresponding fasteners 57 on the delivery device 50, which enable controlled and radially symmetric deployment of the prosthetic heart valve 30. In this embodiment, the packaging 1200 housing the prosthetic heart valve 30 can be sterilized with gamma radiation or other forms of sterilization. Once the packaging 1200 is secured to the delivery device 50, the connected packaging 1200 and delivery device 50 can be further sterilized so that the prosthetic heart valve 30 and delivery device 50 can be manufactured in separate locations while minimizing bioburden concerns.

Turning now also to FIGS. 15A-15D, which illustrate an alternate packaging 1300 for a prosthetic heart valve or other implant (not shown; see, e.g., the prosthetic heart valve 30) and at least a portion of a delivery device (also not shown; see, e.g., the shaft assembly 56). The packaging 1300 includes a container 1302 made of a non-permeable material, such as one of those disclosed above, that can house the prosthetic heart valve loaded onto the portion of a delivery device. The container 1302 can optionally include a vent (not visible) that has a high IP rating to retain moisture within the container 1302 but is suitable for gas-based or radiation-based sterilization techniques. The container 1302 of this embodiment includes a first portion 803 that can be selectively secured to a second portion 1313 via threading or the like. A removable cover 1310 is connected to the second portion 1313. The cover 1310 can be arranged and configured to screw on to the second portion 1313, for example, to generally seal in air and retain moisture within the container 1302 when the packaging 3000 is operatively assembled as is shown in FIG. 15A and a portion of a delivery device (e.g., the shaft assembly 56) is positioned within an aperture 1324 formed by the cover 3010, seal 1328 and second portion 1313. In this embodiment, the packaging 1300 can include one or more Tyvek® (flashspun high-density polyethylene fibers) seals 1330, 1370, 1372 to seal joints at interconnected elements. For example, one Tyvek® seal 1330 can optionally be provided at the threaded connection between the first portion 1303 and the second portion 1313. A second Tyvek® seal 1370 can optionally be provided at the connection between the second portion 1313 and the cover 1310. In addition, one Tyvek® seal 1372 can optionally be provided between the second portion 1313 and the seal 1328. The container 1302 can also include a compartment (not visible, e.g., within the first portion 1303) for the placement of hydrogel, in any of the ways described with other embodiments for the same purpose of regulating humidity within the container 1302.

Although the present disclosure has been described with reference to preferred embodiments, workers skilled in the art will recognize that changes can be made in form and detail without departing from the spirit and scope of the present disclosure.

What is claimed is:

1. A packaged prosthetic heart valve, the packaged prosthetic heart valve comprising:
   a prosthetic heart valve; and
   a container including a first compartment housing the prosthetic heart valve and a second compartment housing a hydrogel; wherein a semi-permeable membrane separates the first and second compartments and the semi-permeable membrane further separates the hydrogel from the first compartment.

2. The packaged prosthetic heart valve of claim 1, wherein the container includes an opening and a permeable membrane compatible with EtO sterilization of the prosthetic heart valve positioned over the opening.

3. The packaged prosthetic heart valve of claim 1, wherein the container further includes a hinged cage positioned around the prosthetic heart valve.

4. The packaged prosthetic heart valve of claim 1, wherein the hydrogel is provided in the form of a sheet, pad or beads.

5. The packaged prosthetic heart valve of claim 1, wherein the container is formed by a double wall, which defines the second compartment.

6. The packaged prosthetic heart valve of claim 1, wherein the hydrogel is loaded with glycerol.

7. The packaged prosthetic heart valve of claim 1, wherein the prosthetic heart valve is secured to a portion of a delivery device that is also at least partially housed in the first compartment.

8. The packaged prosthetic heart valve of claim 7, further comprising a third compartment housing additional hydrogel.

9. The packaged prosthetic heart valve of claim 7, wherein the second compartment is proximate the prosthetic heart valve.

10. The packaged prosthetic heart valve of claim 7, further comprising clips securing the portion of the delivery device to the first compartment.

11. The packaged prosthetic heart valve of claim 7, wherein the container includes a channel in which the portion of the delivery device is positioned; wherein the channel is separated from the second compartment.

12. The packaged prosthetic heart valve of claim 7, wherein the container includes first and second hingedly connected portions.

13. The packaged prosthetic heart valve of claim 12, further comprising a seal proximate an interface between the first compartment and the portion of the delivery device.

14. The packaged prosthetic heart valve of claim 7, wherein the container includes first and second portions; wherein the first portion includes a removable cover.

15. The packaged prosthetic heart valve of claim 14, wherein the cover includes two pieces that are snap fit around the portion of the delivery device.

16. The packaged prosthetic heart valve of claim 14, further comprising a seal interfacing between an aperture in the cover and the portion of the delivery device.

17. The packaged prosthetic heart valve of claim 7, wherein the container includes first and second portions that are threadably secured to each other.

18. The packaged prosthetic heart valve of claim 7, further comprising a porous window/vent.

19. The packaged prosthetic heart valve of claim 1, wherein the container includes two portions of material sealed together to enclose the prosthetic heart valve.

20. The packaged prosthetic heart valve of claim 19, wherein at least one tether is connected to the prosthetic heart valve and extends from the container.

* * * * *